(12) United States Patent
Randolph et al.

(10) Patent No.: US 6,349,443 B1
(45) Date of Patent: Feb. 26, 2002

(54) BOTTLE/NIPPLE CLEANING DEVICE

(75) Inventors: Ross Steven Randolph, Rockaway; Francis X Manganiello, Pompton Plains, both of NJ (US)

(73) Assignee: Playtex Products, Inc., Westport, CT (US)

(*) Notice: Subject to any disclaimer, the term of this patent is extended or adjusted under 35 U.S.C. 154(b) by 0 days.

(21) Appl. No.: 09/634,902

(22) Filed: Aug. 9, 2000

Related U.S. Application Data

(60) Provisional application No. 60/148,103, filed on Aug. 10, 1999, and provisional application No. 60/206,126, filed on May 22, 2000.

(51) Int. Cl.⁷ .................................................. A47L 17/00
(52) U.S. Cl. .......................... 15/114; 15/106; 15/164; 15/176.6; 15/211; D4/133
(58) Field of Search ................................ 15/65, 75, 106, 15/114, 118, 164, 176.1, 176.6, 211; D4/128, 133

(56) References Cited

U.S. PATENT DOCUMENTS

| 934,613 A | 9/1909 | Holm et al. |
|---|---|---|
| 944,262 A | 12/1909 | Friedrich |
| 1,101,671 A | 6/1914 | Ward |
| 1,804,240 A | 5/1931 | Welsh |
| 1,951,023 A | 3/1934 | Josselyn |
| 2,026,638 A | 1/1936 | Kingman |
| 2,257,911 A | 10/1941 | Kraft |
| 2,303,660 A | 12/1942 | Schickel |
| 2,375,263 A | 5/1945 | Upper |
| 2,601,771 A | 7/1952 | Cameron |
| 2,744,281 A | 5/1956 | Zinggeler |
| 2,755,497 A | 7/1956 | Greacen, Jr. |
| 2,792,579 A | 5/1957 | Roy |
| 2,793,477 A | 5/1957 | Gray |
| 2,803,029 A | 8/1957 | Brady |
| 2,893,029 A | 7/1959 | Vosbikian |
| 2,916,754 A | 12/1959 | Zottola |
| 2,941,225 A | 6/1960 | Paul |
| 2,955,056 A | 10/1960 | Knox |
| 3,073,716 A | 1/1963 | Gilchrist |
| 3,105,263 A | 10/1963 | Ginter |
| 3,148,404 A | 9/1964 | Jensen |
| 3,174,174 A | 3/1965 | Dengler |
| 3,231,921 A | 2/1966 | Cuervo |
| 3,317,944 A | 5/1967 | Napier, Sr. |
| D211,397 S | 6/1968 | Nika |
| 3,402,009 A | 9/1968 | Sawyer |
| 3,414,928 A | 12/1968 | Lemelson |
| 3,491,397 A | 1/1970 | Hesener |
| 3,607,159 A | 9/1971 | Haywood |
| 3,611,468 A | 10/1971 | Michael |

(List continued on next page.)

FOREIGN PATENT DOCUMENTS

| FR | 826.644 | 4/1938 |
|---|---|---|
| FR | 1.115.137 | 4/1956 |
| FR | 1.562.771 | 4/1969 |
| FR | 2.210.377 | 7/1974 |
| GB | 950702 | 2/1964 |
| GB | 1188381 | 4/1970 |

*Primary Examiner*—Terrence R. Till
(74) *Attorney, Agent, or Firm*—Ohlandt, Greeley, Ruggiero & Perle, LLP

(57) ABSTRACT

A cleaning device has a handle. The handle has a wall with a distal end with a recess extending axially into the handle, and an elongated nipple brush secured in the recess, such that the distal end of the brush extends axially beyond the distal end of the handle. The nipple brush can be housed in a core having a main body with a sponge secured thereto and an extension with opposed depressible tabs that can be inserted into the recess of the handle. Each tab has one or more protuberances that are biased to seat in opposed apertures in the wall of the handle. The core has an axial channel. When the extension of the core is inserted in the recess and attached to the handle, there is provided a cleaning device with a sponge at one end of the handle and a nipple brush housed in the channel of the core.

35 Claims, 13 Drawing Sheets

U.S. PATENT DOCUMENTS

| | | |
|---|---|---|
| 3,626,023 A | 12/1971 | Brizgy |
| 3,629,896 A | 12/1971 | Sirnec |
| 3,646,628 A | 3/1972 | Halford |
| 3,694,845 A | 10/1972 | Engelsher |
| 3,925,526 A | 12/1975 | Haas |
| 3,931,429 A | 1/1976 | Austin |
| 3,965,521 A | 6/1976 | Wardell |
| 3,979,163 A | 9/1976 | Beard |
| 3,998,012 A | 12/1976 | Ness |
| 4,000,028 A | 12/1976 | Hoey |
| 4,023,677 A | 5/1977 | Wittner et al. |
| 4,055,029 A | 10/1977 | Kalbow |
| 4,055,897 A | 11/1977 | Brix |
| 4,098,944 A | 7/1978 | Pollock |
| 4,130,683 A | 12/1978 | Michel et al. |
| 4,180,427 A | 12/1979 | Bertsch |
| 4,190,921 A | 3/1980 | Rose |
| 4,232,128 A | 11/1980 | Michel et al. |
| 4,264,337 A | 4/1981 | Fenster et al. |
| 4,279,953 A | 7/1981 | Barden et al. |
| D269,917 S | 7/1983 | Spann |
| 4,517,702 A | 5/1985 | Jackson |
| 4,574,415 A | 3/1986 | Vitonis |
| 4,784,647 A | 11/1988 | Gross |
| 4,800,116 A | 1/1989 | Ventimiglia et al. |
| 4,856,136 A | 8/1989 | Janssen |
| 4,940,631 A | 7/1990 | Colin et al. |
| 4,975,229 A | 12/1990 | Kita et al. |
| 4,991,362 A | 2/1991 | Heyer et al. |
| 5,010,615 A | 4/1991 | Carter |
| 5,033,155 A | 7/1991 | Klotz |
| D321,989 S | 12/1991 | Wilson |
| 5,071,061 A | 12/1991 | Willis |
| 5,077,857 A | 1/1992 | Sellers |
| D335,223 S | 5/1993 | Shumway et al. |
| D336,160 S | 6/1993 | Shumway et al. |
| 5,214,820 A | 6/1993 | Shumway et al. |
| 5,253,386 A | 10/1993 | LaLonde |
| 5,336,330 A | 8/1994 | Shumway et al. |
| 5,339,480 A | 8/1994 | Murg et al. |
| 5,341,538 A | 8/1994 | Banome |
| 5,447,572 A | 9/1995 | LaClair |
| 5,488,747 A | 2/1996 | Woodhouse |
| 5,491,863 A | 2/1996 | Dunn |
| 5,522,110 A | 6/1996 | Borofsky |
| D375,595 S | 11/1996 | Shumway et al. |
| 5,621,941 A | 4/1997 | Liu |
| 5,636,400 A | 6/1997 | Young |
| 5,709,003 A | 1/1998 | Batch |
| 5,875,510 A | 3/1999 | Lamond et al. |
| D408,106 S | 4/1999 | Cousin et al. |
| 5,899,893 A | 5/1999 | Dyer et al. |

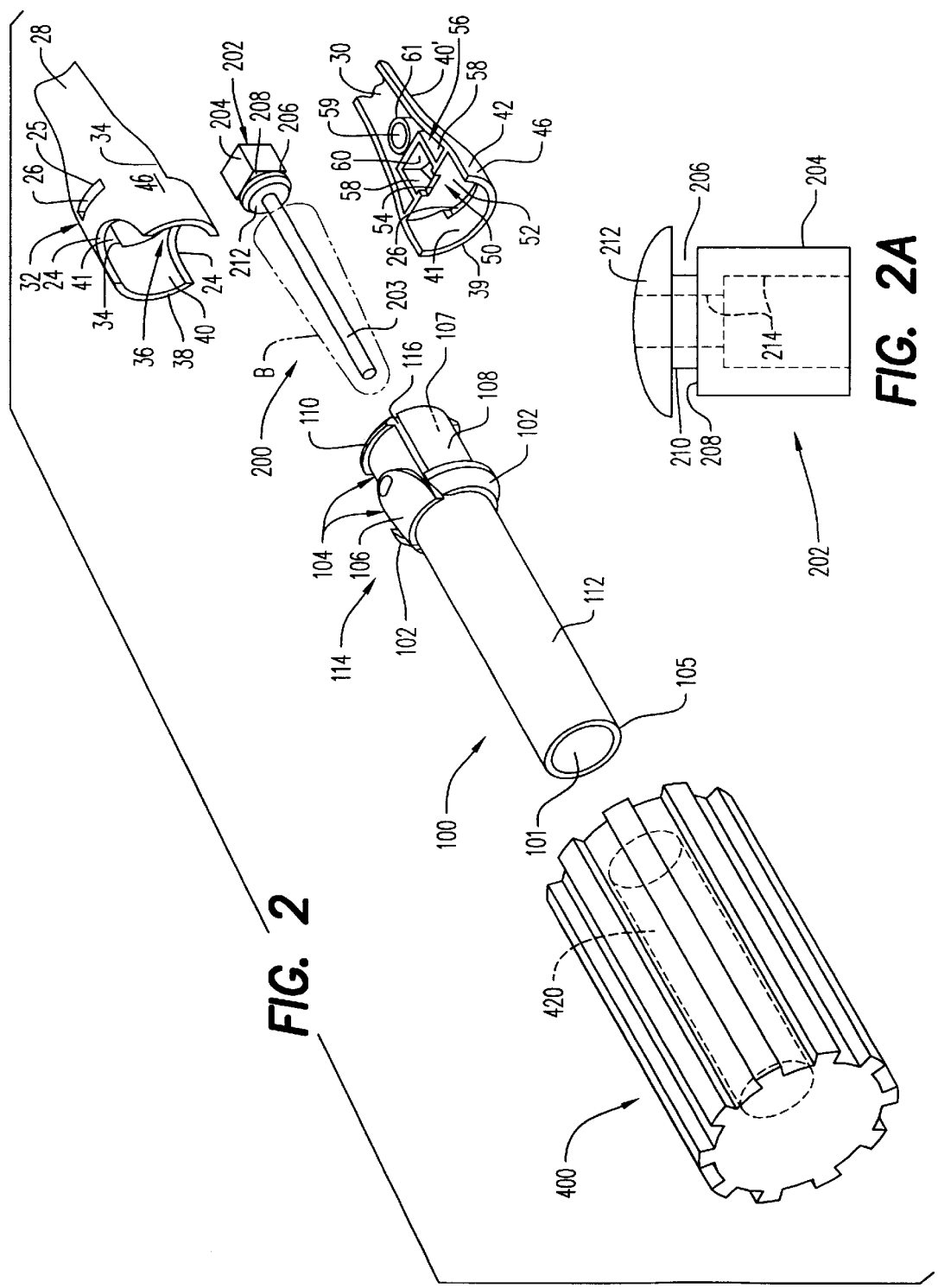

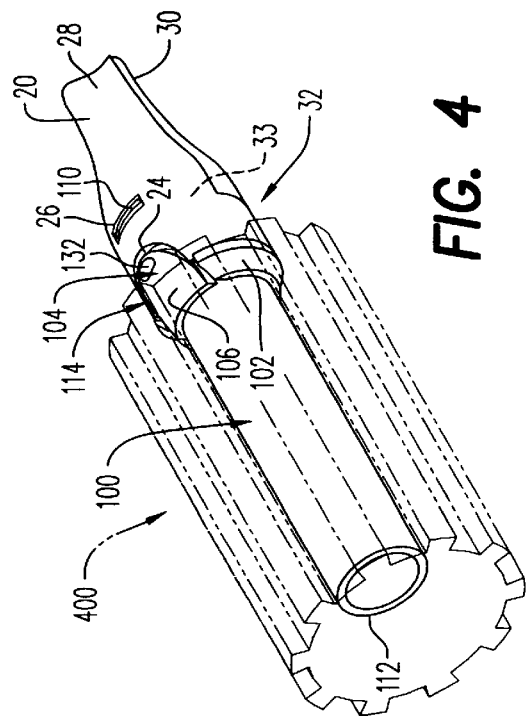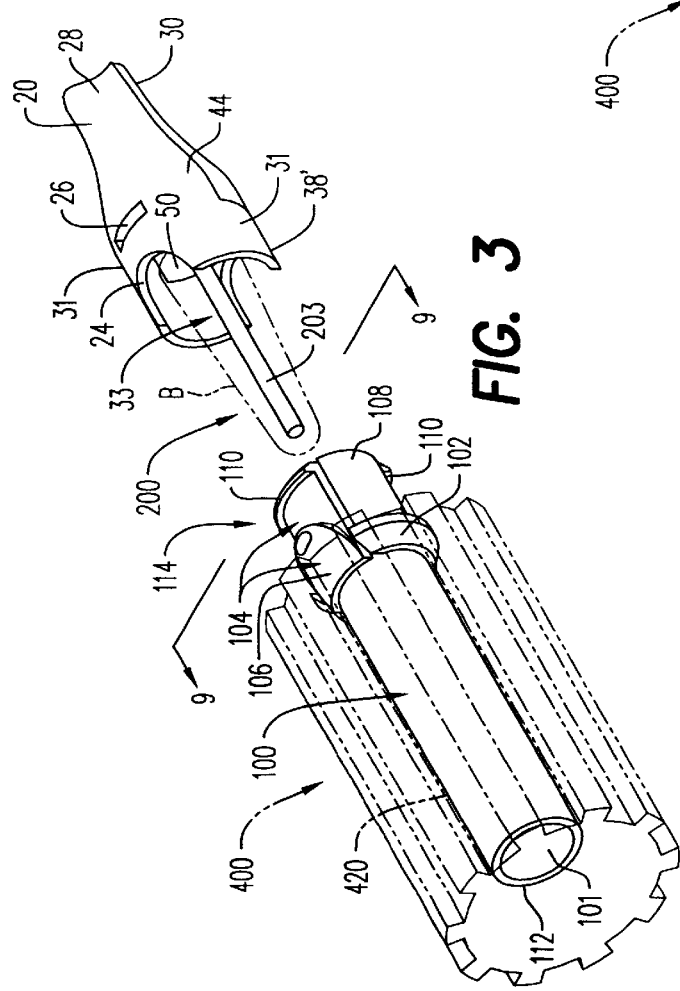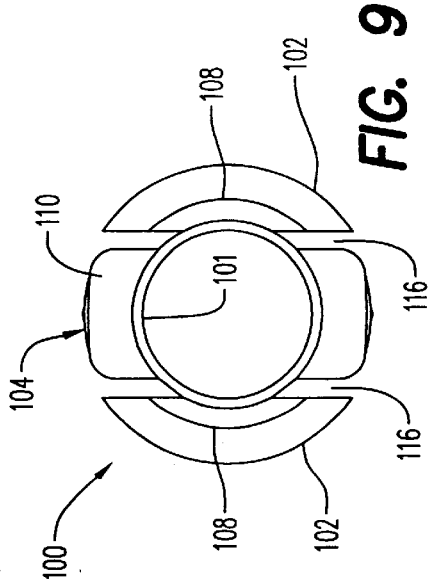

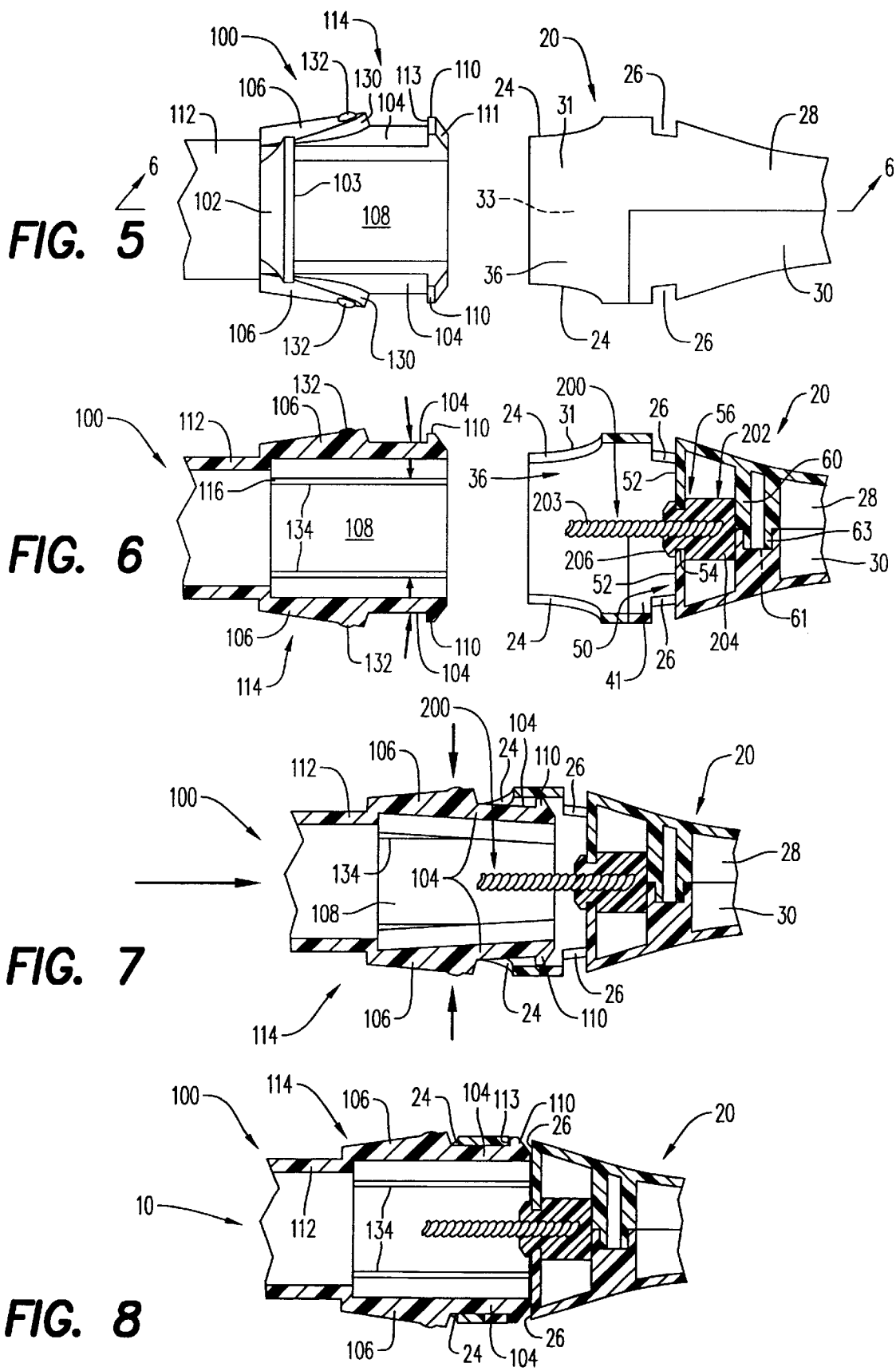

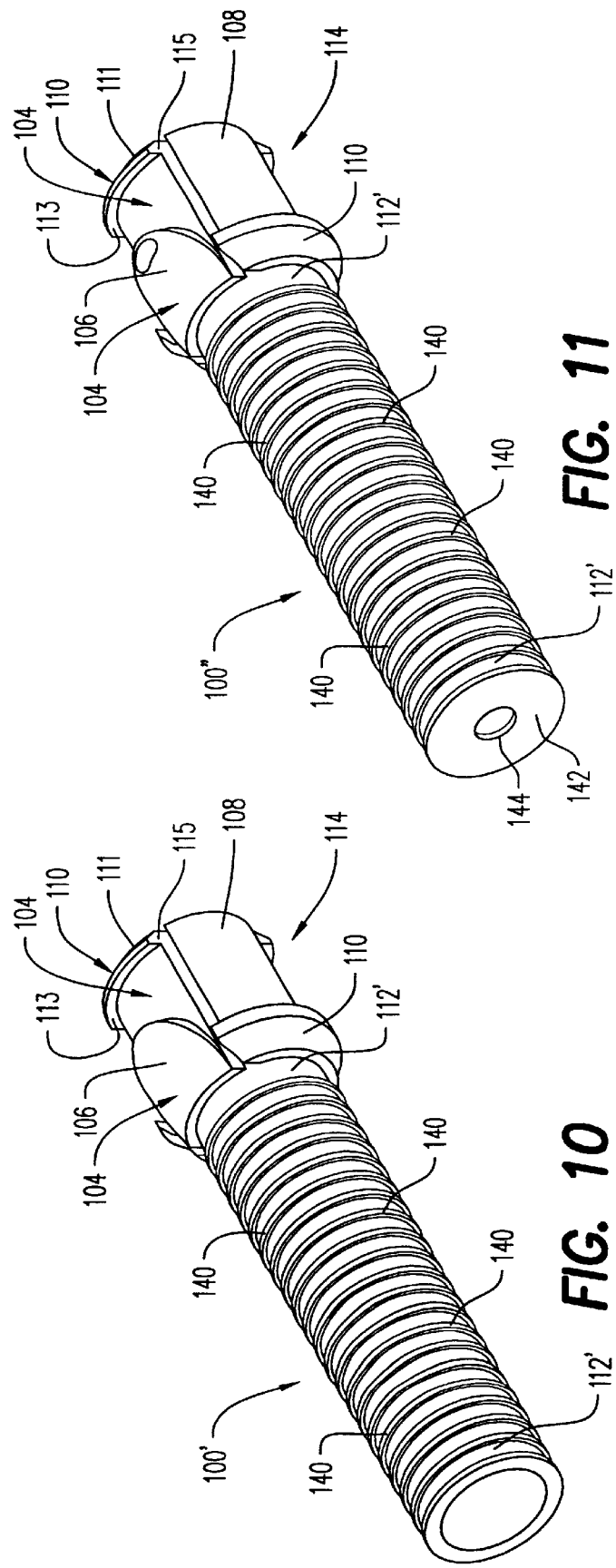

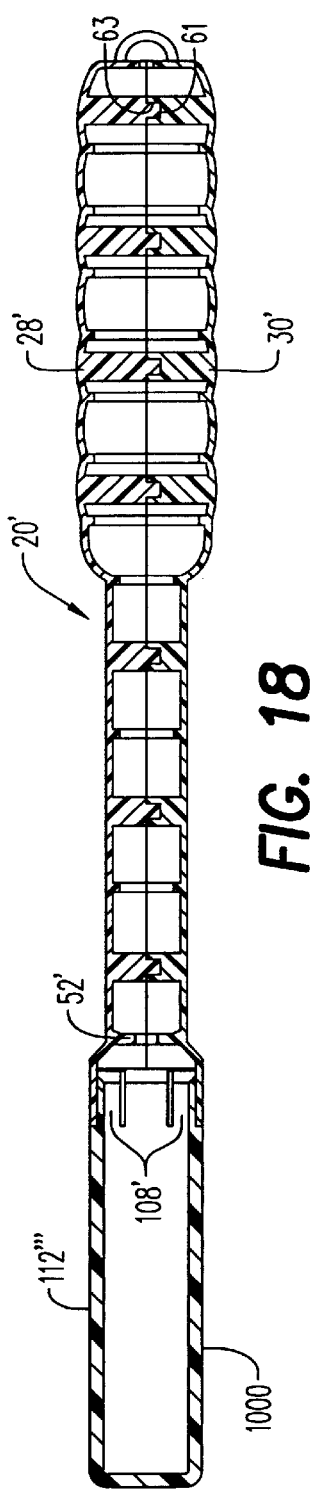
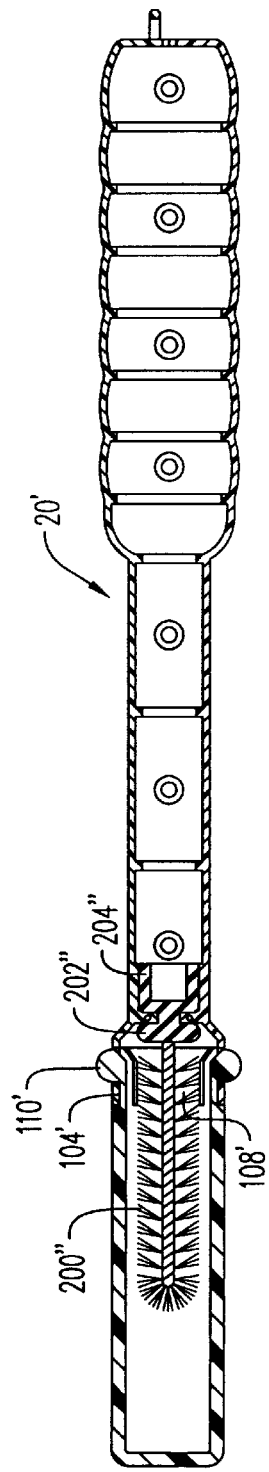
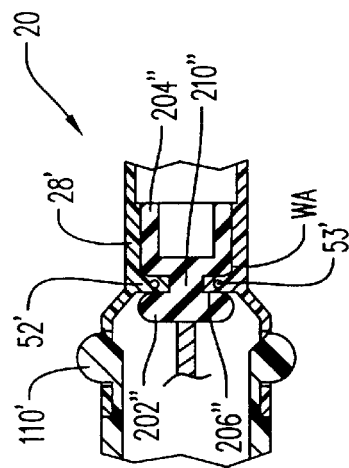

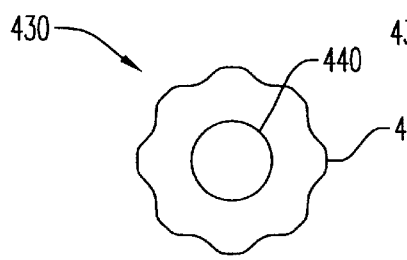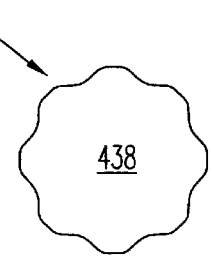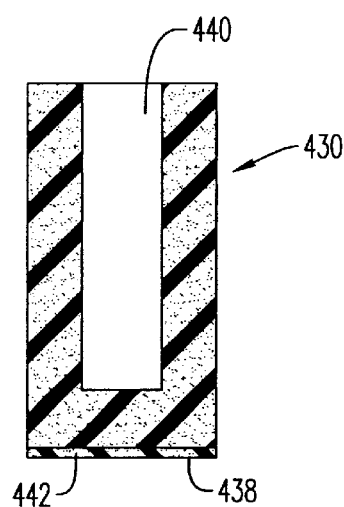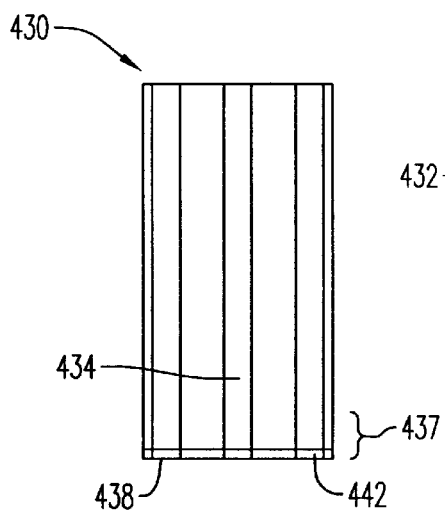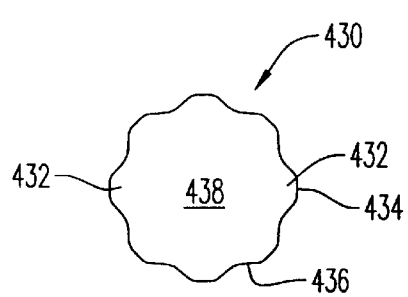

BOTTLE/NIPPLE CLEANING DEVICE

This application claims the benefit of U.S. Provisional Application No. 60/148,103, filed Aug. 10, 1999, and of U.S. Provisional Application No. 60/206,176, filed May 22, 2000.

BACKGROUND OF THE INVENTION

1. Field of the Invention

The present invention relates to a cleaning device and, more particularly, to a device for cleaning bottles, especially baby bottles and nipples for such bottles.

2. Description of the Prior Art

U.S. Pat. No. 5,214,820 to Shumway, et al., titled Dish Scrubber, is directed to a bottle brush having a scrubber. This patent is incorporated herein by reference. The assignee of the present invention is licensed under U.S. Pat. No. 5,214,820.

SUMMARY OF THE INVENTION

It is an object of the present invention to provide a cleaning device.

It is another object of the present invention to provide a cleaning device that has a handle and a sponge attached to the handle for cleaning the interior of a baby or infant or other bottle.

It is still another object of the present invention to provide such a cleaning device in the form of a bottle brush that has a nipple brush attached to the handle for cleaning a nipple.

It is a further object of the present invention to provide such a cleaning device in the form of a bottle brush that has a handle attaching mechanism for removably attaching the sponge to the handle.

It is a further object of the present invention to provide a cleaning device having a nipple cleaning element secured to a handle and a container cleaning element removably attached to the handle such that the nipple cleaning element is housed interior of the container cleaning element while the latter is attached to the handle.

These and other objects of the present invention are achieved by, and the invention is directed to a bottle/nipple cleaning device that has a handle, a sponge for cleaning the interior of a baby, infant or other bottle, and a nipple brush attached to the handle for cleaning a nipple. A hollow core is inserted into an elongated hole or bore formed into the sponge, or into another hole-providing device such as another core positioned in, and secured to the interior of the sponge. The core has a handle attaching mechanism for removably attaching the sponge and handle attaching mechanism of the core to the handle. The core attaching mechanism includes a core extension that protrudes from the sponge when the main body of the core is mounted in and secured to the sponge. The extension has a pair of opposed tabs, preferably integral with the core extension at one end of the tab and free at the other end of the tab. The core extension or at least a portion of it fits into the end of the handle. The end of the handle preferably has two arcuate cutouts therein to receive portions of the tabs. Each tab has a raised portion, preferably a pad extending from the sponge end of the core extension and that terminates preferably in an arcuate edge part-way along the tab, and a raised ridge at the far end of the tab. The end portion of the handle has opposed slots therein. Each slot is adapted to receive the ridge of a tab. As the extension and tabs or as the tabs are inserted axially into the open end of the handle, the preferably beveled, rounded or angled leading edges of the ridges engage the distal or terminal end and/or an interior surface of the wall of the handle. This depresses the ridges and tabs inwardly toward each other until, with rotational movement, if necessary, the raised portions or pads of the tabs enter the cutouts and the ridges move outwardly into their respective slots. This engages and secures the core extension to the handle. The tabs are depressable inwardly toward each other against the bias of the plastic or polymeric rigid structural material of which they are made. The bias forces the ridges of the tabs outward into the slots to maintain the securement of the core extension to the handle. Movement of the tabs inward against the bias permits the tabs to be removed from the cutouts and the ridges from the slots and allows the core and sponge to be removed from the handle.

The above and other objects of the invention are also achieved by, and the invention is also directed to a cleaning device that is comprised of a handle and a nipple cleaning element. The handle has a proximal end for being grasped by a user, a distal end and a distal end portion, the distal end and distal end portion having a wall, a recess defined by the wall, and mounting means located in the recess for mounting a nipple cleaning element to the mounting means.

The nipple cleaning element is suitable for cleaning the interior of a nipple of the type used in connection with a baby bottle. The nipple cleaning element is comprised of a proximal end, a distal end, and means for securing the nipple cleaning element to the mounting means of the handle such that the proximal end of the nipple cleaning element is located in the recess of the handle and the distal end of the nipple cleaning element protrudes beyond the distal end of the handle.

The wall of the distal end portion of the handle can have an inside surface and a plurality, e.g., at least one pair of opposed reliefs that extend radially outwardly into the inside surface of the wall. The reliefs can be selected from the group consisting of grooves, apertures, e.g. slots and/or cutouts, and a combination of grooves and apertures. The wall can have a pair of opposed apertures that extend in an axial direction through the wall. The axially extending apertures can be a pair of opposed cutouts, each cutout having an open entrance end at the distal end of the handle and that extends in a proximal direction axially along a portion of the wall. The distal end portion of the wall of the handle can have a pair of opposed reliefs, and the pair of opposed cutouts and the pair of opposed reliefs can be axially aligned with each other and axially spaced from each other along the wall of the handle.

The objects of the invention are also achieved by, and the invention is also directed to a cleaning member for use with the handle of a cleaning device. The cleaning member is comprised of a cleaning element having an elongated axial dead end bore, and an elongated core. The core can include an elongated main body having a first end and that is disposed in the bore and is secured to the cleaning element, and an extension that extends from and beyond the main body in an axial direction opposite to the first end. The extension can have an open end, an elongated channel that extends from the open end axially into the interior of the extension, and a plurality of opposed axially elongated tabs, each having an outer surface and a free end. Each of the opposed tabs has a normal position, and is movable from the normal position inward toward the channel and biased to return to the normal position. Each of the opposed tabs includes at least one protuberance that extends outwardly beyond the outer surface of the tab. The at least one protuberance can extend in an axial direction on the tab, and it can comprise a pad, and the at least one protuberance can extend in a transaxial direction on the tab and it can comprise a ridge.

The outer surface of the main body of the core can have a plurality of outwardly extending ribs that are axially spaced from one another to assist in securing the cleaning element to the core. The main body can have a wall with a hole in it that communicates with the channel of the core to permit drainage of liquid from the channel.

The objects of the invention are also achieved by and the invention is further directed to a cleaning device that is comprised of a handle and a cleaning member that is removably attached to the handle. The handle can have a proximal grasping end, a distal end, a distal end portion, and a wall, the wall having an interior surface that defines a recess that extends from the distal end axially into the distal end portion of the handle. The interior surface of the wall can have a plurality of reliefs therein. The cleaning member can be comprised of a core that is removably attached to the handle, and an elongated first cleaning element that is secured to the core. The core can have a main body and an extension that extends from the main body and is disposed in the recess of the handle. The extension has a plurality of axially extending radially outwardly biased tabs, each having at least one protuberance that fits in and frictionally engages a relief in the interior surface of the wall of the handle, to removably attach the cleaning member to the handle. The plurality of tabs are movable inwardly against their bias to disengage the protuberances from the reliefs and permit removal of the cleaning element from the handle.

The first cleaning element can be a cylindrical sponge that is suitable for cleaning the interior of a container for feeding liquid to a baby. The handle can include an elongated second cleaning element having a distal end and a proximal end, wherein the proximal end is secured to the handle within the recess such that the distal end of the cleaning element protrudes from the distal end of the handle, and is housed in the channel of the core when the cleaning member is attached to the handle. The second cleaning element of the handle can be a brush that is suitable for cleaning the interior of a nipple for feeding a baby.

The pair of opposed reliefs can be cutouts in the distal end of the wall of the handle and that extend in an axial direction long the wall and preferably are conically shaped when seen in plan view, and/or the reliefs can be slots that extend in a transaxial direction through the wall of the handle and preferably are rectangular when seen in plan view. The cutouts and slots can be axially aligned with each other and axially spaced from one another along the wall of the handle.

The at least one protuberance on each of the tabs can comprise a pad that extends in an axial direction along the tab and preferably is conically shaped when seen in plan view, and/or the at least one protruberance can comprise a ridge that extends in a transaxial direction across the tab and preferably is rectangular when seen in plan view.

Each of the plurality of opposed tabs preferably includes two protuberances, one a transaxial ridge, and another an axial pad. Each of the plurality of opposed tabs preferably has a proximal free end, and a distal end that is joined to the main body of the core, wherein the at least one transaxial ridge is located adjacent the free end of the opposed tab, and the at least one axial pad is located adjacent the distal end of the tab. Preferably the ridge and pad of a tab are axially aligned, and the transaxial lengths of the ridges of the tabs are shorter than the transaxial lengths of the open entrance ends of the cutouts. The ridges can have leading edges facing away from the main body and that are adapted to move axially into and fit into the open entrance ends of the cutouts, such that when the opposed tabs of the extension of the core are aligned with the open entrance ends of the cutouts of the handle and the core and the handle are moved toward one another, the ridges enter the cutouts such that the edges of the cutouts engage and depress the ridges and the tabs inward toward the channel to enable the ridges to enter the recess and slidingly engage the interior surface of the wall of the handle until the ridges move outwardly into and seat in the slots and the pads of the tabs enter into and seat in the cutouts of the handle, to removably attach the core of the cleaning element to the handle. Preferably the ridges have surfaces and portions that are chamfered, and these chamfered surfaces and portions and the conically shaped pads and cutouts allow the core to be manually rotated relative to the handle to cause the interior surface of the wall of the handle to ride over the pads and the ridges, depress the opposed tabs toward the channel and allow removal of the core from the handle without need of direct manual depression of the pads of the opposed tabs.

The foregoing and other objects and advantages of the present invention will be more apparent from the following detailed explanation of the preferred embodiments of the invention taken in connection with the drawings.

BRIEF DESCRIPTION OF THE DRAWINGS

FIG. 2 is an exploded perspective view, with portions broken away, of the cleaning device of FIG. 1;

FIG. 2A is a front elevational view of the nub of the nipple brush;

FIG. 3 is an exploded perspective view with portions broken away of portions of FIG. 2;

FIG. 4 is a perspective view, with portions broken away, of the components of FIG. 3 after they have been assembled;

FIG. 5 is a side elevational view, with portions broken away, of the proximal end portion of the core axially aligned with terminal end of the assembled handle of FIG. 1;

FIG. 6 is a vertical sectional view, with portions broken away, taken through the core and handle of FIG. 5;

FIG. 7 is a vertical sectional view similar to that of FIG. 6, that shows the extension of the core being mounted into the handle;

FIG. 8 is a vertical sectional view as in FIG. 7 showing the core secured to the handle;

FIG. 9 is an end view of the extension of the core of FIG. 3.

FIG. 10 is a perspective view of an alternative embodiment of the core of the invention.

FIG. 11 is a perspective view of another embodiment of the core of the invention.

FIG. 18 is a horizontal sectional view, with portions not shown, as would be seen along line 18—18 through a cleaning device such as shown FIG. 12 and having a core as shown in FIG. secured thereto.

FIG. 19 is a vertical sectional view, with portions not shown, of a cleaning device of the invention.

FIG. 19A is an enlarges view of a portion of FIG. 19.

FIGS. 25 through 28 show the preferred embodiment of the sponge of the cleaning member of the cleaning device of the invention.

DETAILED DESCRIPTION OF THE INVENTION

Figure 1:
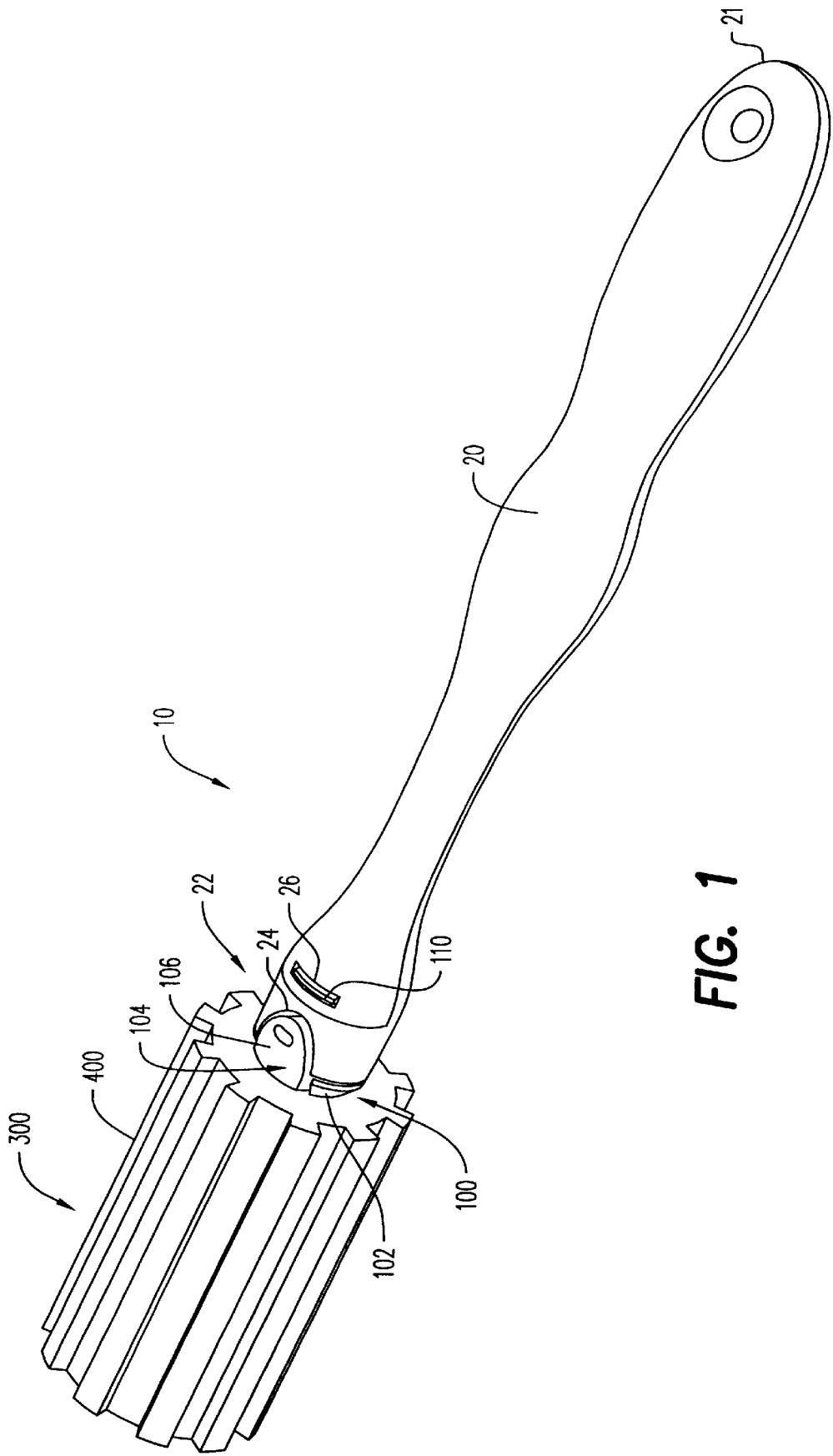
FIG. 1 is a perspective view of the cleaning device of the present invention.

Referring to the drawings and, in particular to FIG. 1, there is provided a preferred embodiment of the assembled cleaning device of the invention, generally represented by reference numeral 10. The device 10 has a handle 20 with a proximal end 21 for being grasped by a user, and a distal end 22 to which is attached a cleaning member 300. Cleaning member 300 is comprised of a cleaning element, here, a cylindrical sponge 400 that is secured to an elongated core 100. The sponge 400 is preferably fluted. It is for cleaning the interior of a container, preferably a baby or other bottle.

FIG. 1 shows a portion of core 100, more particularly a flange 102 thereof, and portions of tabs 104, one of which is shown. More particularly, FIG. 1 shows that tab 104 of core 10 includes a raised pad 106 seated in an arcuate cutout 24 (only one shown) at distal end 22 of handle 20. FIG. 1 also shows raised ridges 110 of tabs 104 seated in slots 26 of handle 20, preferably with raised pads 106 seated in cutouts 24, removably securing a core extension 114 (FIG. 2), core 100 and sponge 400, to handle 20. Cutouts 24 and pads 106 are conically shaped and slots 26 and ridges 110 are rectangularly shaped, when seen in plan view.

Referring to FIG. 2, sponge 400 has an elongated bore, preferably an axial cylindrical dead end bore 420 part way therein. Bore 420 is axially aligned with core 100. Core 100 has an elongated main body 112 disposed in bore 420, a first end 105, and an extension 114 that extends from and beyond main body 112 and has an open end 107. Extension 114 has opposed flanges 102, opposed tabs 104 (one shown) and opposed members 108 (one shown) intermediate and circumferentially spaced from tabs 104 by openings 116 (one shown). Tabs 104 have raised pads 106 and axially aligned raised ridges 110, each molded from and integral with tabs 104.

A nipple cleaning element, preferably a nipple brush 200, is shown axially aligned with core 100. Nipple brush 200 is suitable for cleaning the interior of a nipple of the type used in connection with a baby bottle. Nipple brush 200 has a nub 202, a stem 203 and a bristle or sponge brush B (shown in phantom lines). As shown in Fig. 2A, nipple brush 200 has a proximal end bearing nub 202 and a distal end at the tip of brush B. Nipple brush 200 includes means, e.g. nub 202, for securing nipple brush 200 to handle 20. Nub 202 has a base 204, and annular channel 206 between and formed by the axially interior distal surface 208 of base 204, the cylindrical neck 210, and the proximal surface of a head, here shown as disc 212. The nub 202 has a stepped bore 214 for receiving stem 203 of bristle or sponge brush B therein and for fixedly securing nub 202 thereto. Exploded above and below brush 200 are respective upper and lower halves 28, 30 of handle 20. The upper half 28 has a distal or terminal end portion 32 that is enlarged, a section 34 that is halved, and a section 36 that is circumferentially whole, e.g., annular, i.e. not halved (See, e.g., FIG. 5). The annular section 36 has a pair of opposed reliefs in the form of apertures therein, here including arcuately shaped open-ended cutouts 24. Cutouts 24 have an open entrance end at distal or terminal end 38 and extend from distal end 38 axially into and along distal end portion 32 of wall 40 of hollowed, upper half 28 of handle 20. Handle 20 also has a pair of opposed reliefs in the form of slots 26, one of which extends through wall 40. Preferably the opposed reliefs, here slots 26 and opposed cutouts 24 are axially aligned with each other and axially spaced from each other along wall 40, 40' of handle 20. Lower half 30 of handle 20 has a distal or terminal end portion 42 with an enlarged portion 46 and a distal or terminal end 39. Lower half 30 of handle 20 has a slot 26 extending therethrough. Axially spaced from distal or terminal end 39 of handle 20, and proximal to it, there is mounting means, here including mount 50 for mounting nipple brush 200 to handle 20. Mount 50 comprises a box seat 56 that has a distal end wall 52 orthogonal to outer wall 40' of lower handle half 30, a notch 54 cut or formed into or of distal end wall 52, a pair of axial side walls 58, and end wall 60. In upper half 28 of handle 20, box seat 56 basically has a mirror image of what is shown in lower half 30, and it is dimensioned to snuggly receive block 204 of nub 202 of nipple brush 200. Wall 40' of distal end 39 and distal end portion 42 of lower handle half 30 has an aperture 59 in ring 61 for receiving a pin (not shown) extending from the interior surface of wall 40 of upper handle half 28, for snap fastening the handle halves together to form handle 20 of FIG. 1. The handle halves 28, 30 can be glued or welded together. Wall 40, 40' of handle 20 has an inside surface 41 that defines a recess 33 that extends axially into distal end 38, 39 and distal end portion 32, 42 of handle 20. Mount 50 is located in recess 33.

FIG. 3 shows core 100 seated in bore 420 of sponge 400 and secured to it, e.g. by an adherent, with core extension 114 protruding axially and proximally therefrom. FIG. 3 also shows handle halves 28, 30 secured together such that nipple brush 200 is permanently mounted in recess 33 defined by the wall 40, 40' of assembled distal or terminal end portion 44 of handle 20. The distal or forward end of brush B protrudes from the forward end of handle 20 and is axially aligned with channel 101 in main body 112 of core 100.

As stated above, FIG. 4 is a perspective view, with portions broken away, of the components of FIG. 3 assembled. More particularly, FIG. 4 shows extension 114 of core 100 inserted into recess 33 of terminal end portion 32 of assembled handle 20. Pads 106 of tabs 104 are seated in cutouts 24 of handle 20, and ridges 110 (one shown) are seated in slots 26 (one shown) of handle 20. Nipple brush 200 (not shown) is mounted in handle 20, and the portion of the nipple brush that extends beyond handle 20 extends into proximal open end 107 of core extension 114 and is housed and protected in hollow channel 101 axially interior of main body 112 of core 100.

Cleaning device 10 is assembled by moving either or both of the axially aligned extension 114 of core 100 of FIG. 3 and the brush B of the assembled handle 20 toward each other until the leading or proximal edges 111 of ridges 110 (FIG. 5) engage terminal ends 38, 38' of handle 20, enter its recess 33, and engage the interior surface of the wall of the handle. This moves the tabs and ridges from their normal positions radially inward against their bias until the ridges reach and snap radially outward into opposed slots 26, and pads 106 reach and snap similarly into cutouts 24 in handle 20. Preferably, the transaxial length of ridges 110 is shorter than the transaxial length of the open entrance end of cutouts 24. In such case, the edges of wall 40, 40' of handle 20 that define cutouts 24 engage ridges 110 and depress them into recess 33. Preferably, tabs 104 are axially aligned with cutouts 24 in handle 20 and it and core extension 114 are merely moved axially together. If ridges 110 are not aligned with cutouts 24, 38', ridges 110 will still engage terminal end 38 and the wall of handle 20 and will still depress radially inward toward and enter channel 101 of core 100. Opposed tabs 104 are biased to return to their normal positions. Rotation of core 100 and/or of handle 20 relative to each other may be employed prior to, during or after axial movement to seat ridges 110 in slots 26 and pads 106 in cutouts 24.

FIG. 5 is a side elevational view, with portions broken away, of the proximal end portion of core 100 axially aligned with the terminal end of assembled handle 20. Handle 20 has nipple brush 200 mounted therein, but it is not shown. FIG. 5 shows side members 108 (one shown) that have, and are integral with flanges 102 (one shown) and with main body 112 of core 100. Also shown are opposed tabs 104 whose distal portions are integral with main body 112 of core 100, whose mid-portions have protuberances in the form of axially extending integral raised pads 106, and whose ends or free ends have protuberances in the form of transaxially extending raised ridges 110. Tabs 104 are shown in their normal positions. Flanges 102 preferably do not extend to and are not part of tabs 104. Flanges 102 preferably have a stop wall 103 to prevent further axial movement of core extension 114 into handle 20. Pads 106 of tabs 104 are thinner, i.e., shorter in height, adjacent their distal ends where they rise gradually from the main or outer circumferential surface of tabs 104 and they taper radially outwardly toward the proximal ends of the pads, where they are thicker, i.e. raised higher, relative to the main or outer surface of the tabs. The proximal edges 130 of pads 106 are beveled, in that at least their leading edges are angled to facilitate their slippage and entry into handle 20 and arcuate cutouts 24 in handle 20. The other, non-proximal, edges of pads 106 help to prevent rotational movement between core 100 and handle 20 during normal use of cleaning device 10. Pads 106 are shown having, and can, but preferably do not, have rounded raised bumps 132 thereon that extend above the surface contour of terminal end portion of handle 20. Bumps 132 or the like may be desirable to facilitate contact with and the application of finger pressure to pads 106, if it is desired to design the attaching means to employ a user's fingers to depress tabs 104 radially into the interior of extension 114 of core 100 prior to or during the insertion of a portion of extension 114 into handle 20. It has been found, however, that it is more preferred to not employ bumps 132 and to not design the attaching mechanism to require the application of finger pressure to pinch or depress tabs 104 to insert extension 114 of core 100 into and/or remove it from the handle of the cleaning device of the invention. To attach core 100 to handle 20, it has been found that it is simpler and easier to merely push extension 114 of core 100 into recess 33 of handle 20, preferably with tabs 104 and their ridges 110 axially aligned with cutouts 24, using rotational motion, if necessary, to seat transaxial ridges 110 into transaxial slots 26 and axial pads 104 in axial cutouts 26. Likewise, for removal of core 100 from the handle, it has been found simpler and easier, and preferred, to merely twist or rotate core 100 relative to handle 20 to cause the interior surface of wall 40, 40' to ride over ridges 110 and pads 106 to unseat them from their respective slots 26 and cutouts 24, prior to or during withdrawal of the core from the handle. Direct manual pressure on either or both tabs is unnecessary. FIGS. 9 and 10 show the preferred cores whose pads 106 are without bumps and with ridges 110 that have leading or proximal edges 111, end surfaces 115 and portions that adjoin the end surfaces and leading edges that are chamfered, e.g., rounded, to facilitate movement of ridges 110 axially and/or rotationally into the open entrance ends of cutouts 24 and axially and/or rotationally seating of the ridges in and unseating them from their slots.

FIG. 6 is a vertical sectional view, with portions broken away, taken through core 100 and handle 20 of FIG. 5. FIG. 6 shows opposed tabs 104 in their normal positions before being moved or depressed radially into the interior of core extension 114. FIG. 6 shows the openings 116 between opposed side members 108 and the radially interior lower and upper longitudinal side edges 134 of respective upper and lower tabs 104. This Figure also shows the manner in which nipple brush 200 is mounted in handle 20. More particularly, block or base 204 of nub 202 is seated in box seat 56 with the edges of notch 54 in distal wall 52 seated in and engaged by the surfaces forming channel 206 to prevent nipple brush 200 from moving axially or radially in relation to handle 20. With the respective upper and lower halves 28, 30 of handle 20 assembled as shown by pin 63 of the upper half within and adhered or welded to ring 61 of the lower half, and with mirror images of box seat 56 of mount 50 encompassing and engaging nub 202, nipple brush 200 is permanently fixed to handle 20. Less preferably, the handle halves can be separable or brush 200 can otherwise be removable from the handle.

FIG. 7 is a vertical sectional view similar to that of FIG. 6. FIG. 7 shows extension 114 of core 100 being moved or mounted into handle 20. The proximal ends of opposed tabs 104 having ridges 110 are shown depressed by and sliding axially along the inside surface of the wall of handle 20, prior to ridges 110 reaching slots 26. Longitudinal side edges 134 of tabs 104 are depressed radially within and inwardly beyond the side edges of side members 108 (one shown).

FIG. 8 is a vertical sectional view as in FIG. 7 showing core 100 secured to handle 20. Extension 114 of core 100 has been moved axially further into handle 20 such that pads 106 of tabs 104 are seated in arcuate cutouts 24 of the handle, and ridges 110 are seated in slots 26 of the handle. The spring tension of the molded plastic structural material biases opposed pads 106 and ridges 110 radially outward such that they seat in and preferably frictionally engage their respective cutouts 24 and slots 26. Core 100 and handle 20 are axially and rotationally locked in place mainly by the engagement of vertical edges 113 of ridges 110 of tabs 104 with the edges that define slots 26 in handle 20, desirably by the engagement of edges 130 of pads 106 with the edges that define cutouts 24 in handle 20 and by the spring tension of the material of extension 114, particularly of tabs 104, that maintains these engagements. Core 100 and handle 20 can also be prevented from moving too far relative to each other by engagement of stop walls 103 of flanges 102 of core 100 (FIG. 5) with terminal ends 28, 28' and 30 of handle 20. Core 100 is separated from handle 20 preferably by rotating them relative to each other to move tabs 104 inward against their bias and disengage pads 106 from cutouts 24 and ridges 110 from slots 26, and by simultaneously or subsequently pulling the core and handle axially apart. The sides of pads 106 and the ends or end surfaces of ridges 110 preferably are rounded or beveled to facilitate their intentional rotational removal or disengagement from cutouts 24 and from slots 26. Once these elements are disengaged, brush B can be withdrawn from core 100.

FIG. 9 is an end view of extension 114 of core 100 of FIG. 3. FIG. 9 shows there are openings 116 between the side edges of tabs 104 and side members 108 to allow tabs 104 to flex or bend radially inward toward each other when core 100 is inserted into the distal end of handle 20.

FIG. 10 shows a second embodiment of the core of the invention. More particularly, FIG. 10 shows a core 100' having a main body 112' that is cylindrical and whose outer surface has a plurality of radially outwardly extending annular ribs 140 extending thereabout. Ribs 140 preferably are equally spaced from one another and extend sufficiently from the exterior surface of the main body so as to engage the interior surface of bore 420 of a cleaning element such as sponge 400 of FIG. 1. With or without an adherent, ribs 140 help prevent relative axial movement between and secure a sponge, brush or other cleaning member to core 100'.

FIG. 11 shows the most preferred embodiment of the core of the invention. FIG. 11 shows a core 100" similar to that shown in FIG. 10, except that the main body 112" of core 100" has a wall, preferably an end wall 142, with a hole, preferably hole 144, therethrough. End wall 142 provides support or a back-up wall for the distal end portion of the sponge when the sponge is inserted into a container such as a glass or baby bottle and pressure is axially and rotationally applied to the sponge to scrub the bottom and/or the interior of the bottle. Hole 144 communicates with channel 101, allows water or other liquids or solids that enter the proximal end of the core to escape or drain from the core. In FIGS. 10 and 11, there are no bumps on pads 106 of tabs 104, and the leading or proximal edges 111 and end surfaces 115 of ridges 110 are rounded.

The most preferred core is about 4 inches long, and its main body is about 3 inches long. The outer diameter of the main body including the rib is about 0.87 inch. Each rib is about 0.10 inch high and about 0.030 inch wide. For a core having a main body of about 3 inches in length, preferably there are about 25 ribs spaced about 0.075 inch from each other. Preferably, hole 144 is about 0.25 inch in diameter.

Figure 12:
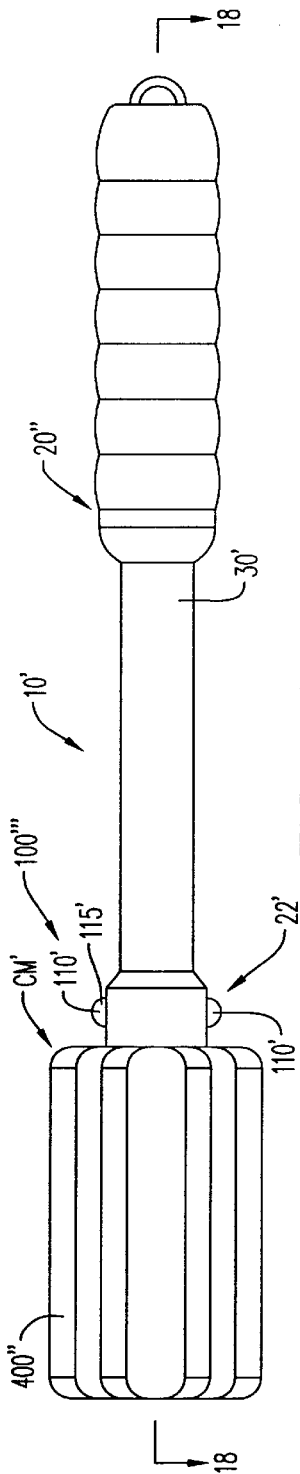
FIG. 12 is a side view of a second embodiment of the cleaning device of the invention.
Figure 13:
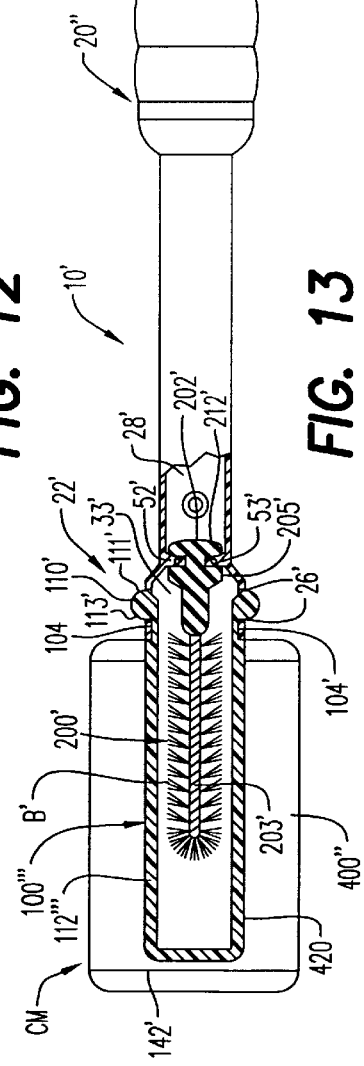
FIG. 13 is a vertical section, with portions broken away, of the cleaning device of FIG. 12.

FIGS. 12 through 16 show a second embodiment of the cleaning device of the invention, generally referred to as 10'. Cleaning device 10' is comprised of a handle 20' having a distal end 22' that is attached to a cleaning member CM by a core 100'". Cleaning member CM is comprised of a sponge 400" that is attached to core 100'" in the manner described above in connection with cleaning device 10 of FIG. 1. Core 100'" has a main body 112'", and at its proximal end, a pair of opposed integral tabs 104', each having a radially outwardly extending ridge, here shown as an elongated bead 110' having rounded leading, trailing and end surfaces 111', 113' and 115'. Although not shown, core 100'" preferably has ribs 140 and its end wall 142', has a hole therein as shown for core 100'" in FIG. 11. Handle 20" is comprised of right and left halves 28', 30', each a mirror image of the other, except that right half 28' has pins 63 and left half has rings 61. The distal or terminal end portion 32' of handle 20" is enlarged and has notches 25' therein (FIG. 15) that, in the assembled handle, form diametrically opposed slots 26' for receiving beads 110' of tabs 104' therein (FIG. 13).

Figure 13A:
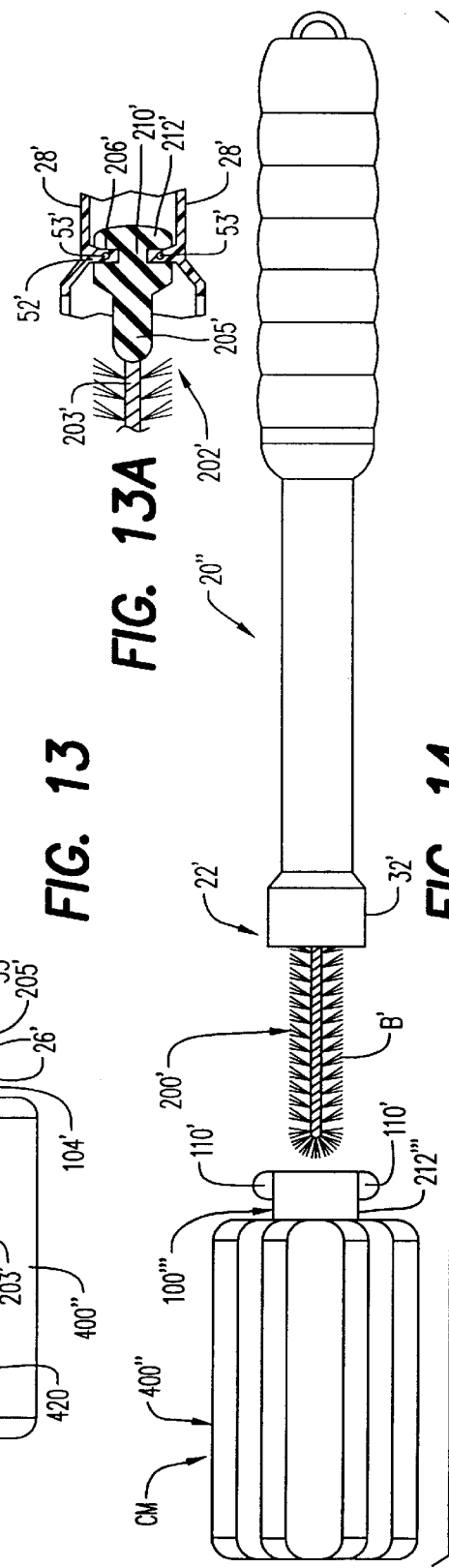
FIG. 13A is an enlarged view of a portion of FIG. 13.

FIG. 13 shows assembled cleaning device 10'". More particularly, FIG. 13 shows that main body 112'" and preferably end wall 142' of core 100'" are adhered to the interior surface of bore 420 of sponge 400", and beads 110' are biased into and seated in slots 26' of distal end portion 32' of handle 20" to thereby removably secure cleaning member CM to handle 20'". FIGS. 13 and FIG. 13A show that distal end 22' and distal end portion 32' of handle 20" have a recess 33' that has means, here shown as a flange 52' extending inward from the interior surface of the wall of the right half 28' of handle 20" and having pins 53' thereon for mating with a holes 55' (FIG. 15) in flange 52' of left half 30' of the handle, for mounting a nipple brush 200' in distal end portion 32' of the handle. Nipple brush 200' is comprised of a nub 202', a stem 203' and a bristle or sponge brush B'. Nub 202' has a body 205', a disc or head 212', and a neck 210' extending between body 205' and head 212'. Between body 212' and head 212' there is a channel 206' for receiving flange 52' therein. FIG. 13 shows that most of nipple brush 200" is housed within and protected by core 100'".

Figure 14:
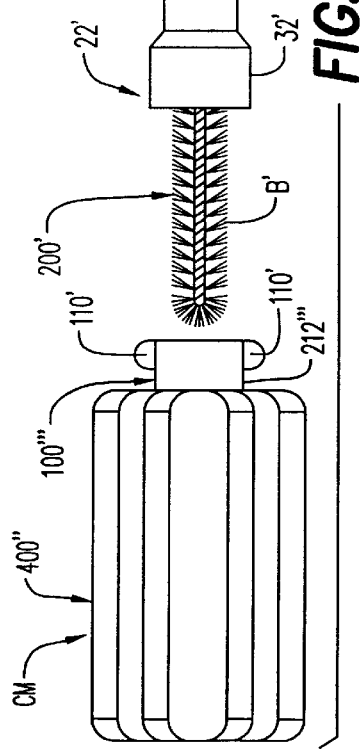
FIG. 14 is a side view of the cleaning device of FIG. 12, with the cleaning member removed from the handle.
Figure 15:
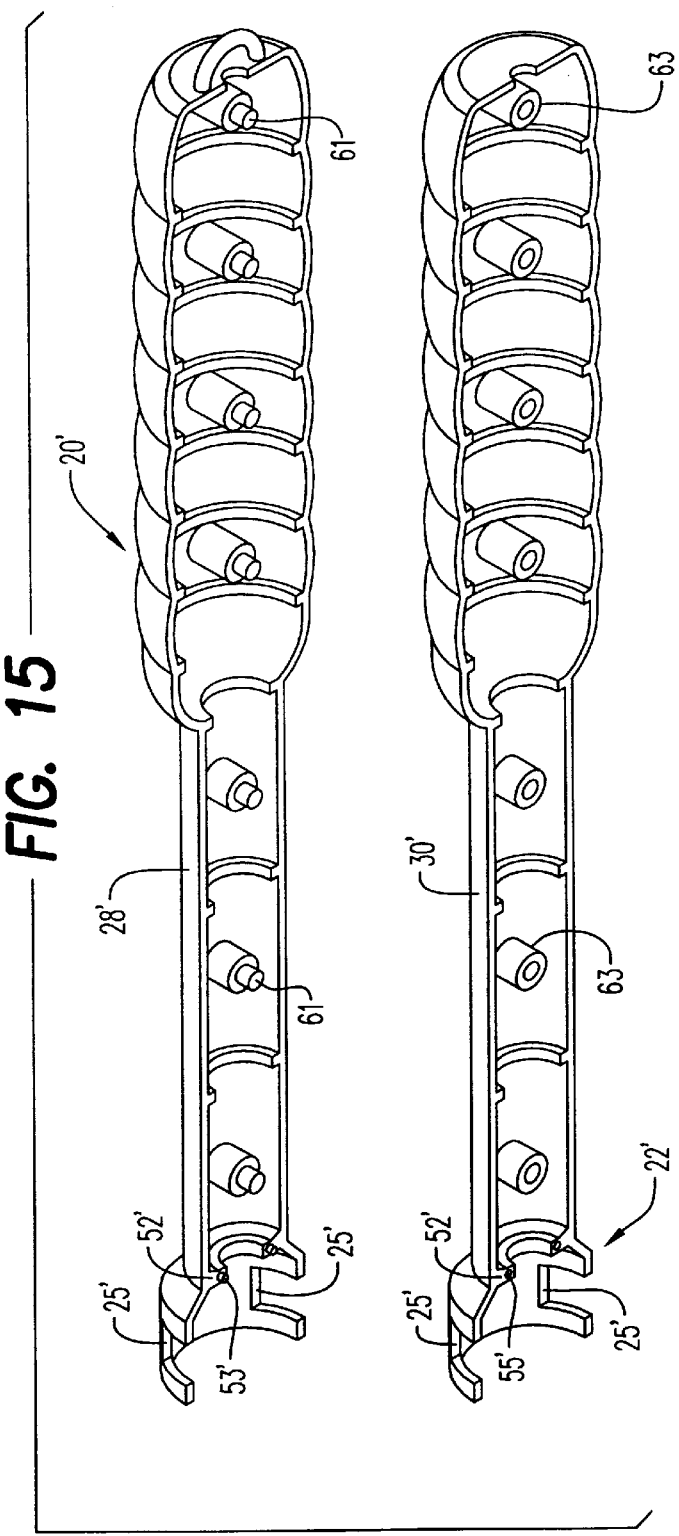
FIG. 15 is an exploded view of the halves of the handle of the cleaning device of FIG. 12.

FIG. 14 shows handle 20" with nipple brush 200' secured thereto, after removal of nipple brush 200" from core 100'". Removal can be effected in a manner described above in connection with removal of brush 200 from core 100.

Figure 16:
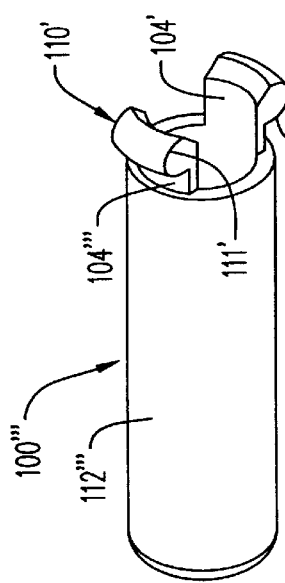
FIG. 16 is a perspective view of a fourth embodiment of the core of the invention, the embodiment that is employed in the cleaning device of FIG. 12.

FIG. 16 shows a perspective view of core 100'" of cleaning device 10'.

Figure 17:
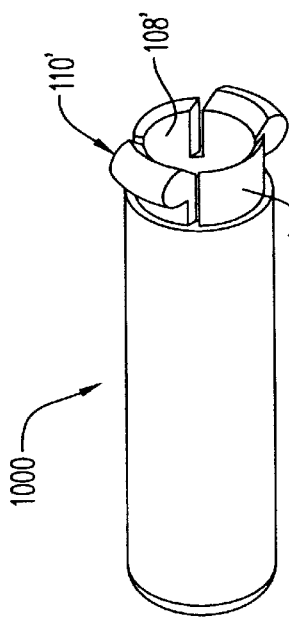
FIG. 17 is a perspective view of a fifth embodiment of the core of the invention.

FIG. 17 shows a fifth embodiment of the core of the invention. FIG. 17 shows a core 1000 like that shown in FIG. 16, except that the core has opposed interstitial side members 108' that are like side members 108 of core 100 shown in FIGS. 2 and 3.

FIG. 18 is a horizontal sectional view as would be seen along line 18—18 of FIG. 12, if a nipple brush was not shown therein and if core 1000 of FIG. 18 were employed instead of core 100'" in cleaning device 10' of FIG. 12. FIG. 18 shows interstitial side member 108' of core 1000 and annular flange 52' of handle 20'.

FIGS. 19 and 19A show alternative structure for mounting a nipple brush to handle 20'. More particularly, FIGS. 19 and 19A show a nipple brush 200" having a nub 202" comprised of a square, hollow base 204", a neck 210" and a channel 206". Base 204" is seated in a squared out wall area WA of handle 20'.

Figure 20:
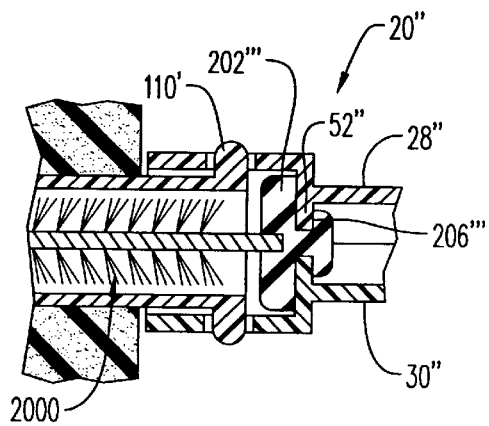
FIG. 20 is an enlarged vertical sectional view similar to those of FIG. 13A and 19A, of an embodiment of the attaching mechanism of the cleaning device of the invention.
Figure 23:
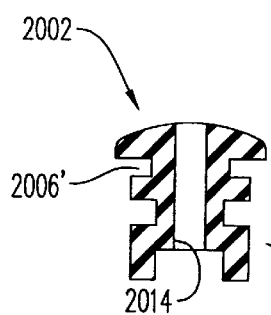
FIGS. 21 through 24 show the most preferred embodiment of the nub of the nipple brush of the cleaning device of the invention.
Figure 21:
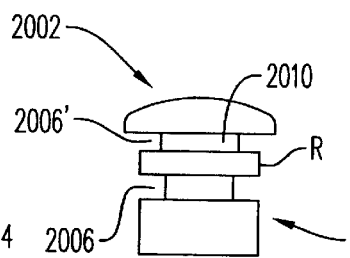
Figure 22:
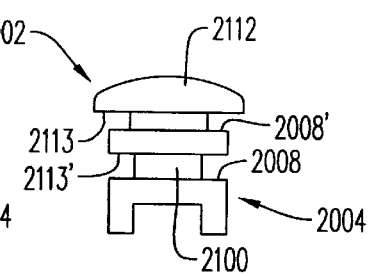
Figure 24:
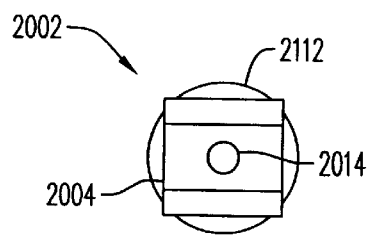
Figure 31:
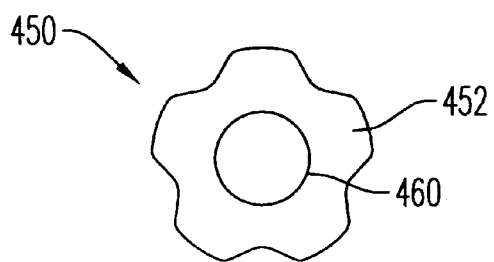
FIGS. 29 through 32 show another embodiment of the sponge of the cleaning member of the cleaning device of the invention.
Figure 29:
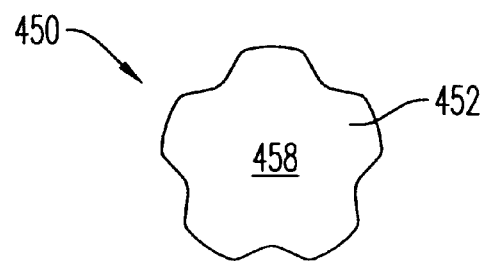
Figure 30:
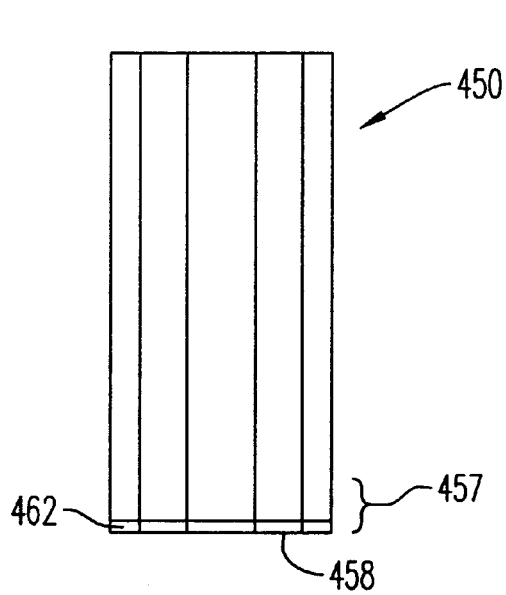
Figure 32:
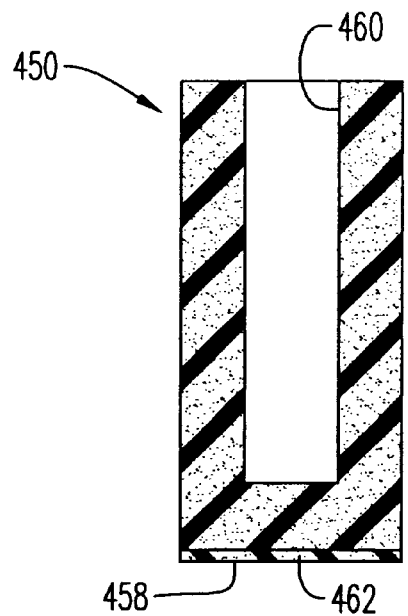
Figure 35:
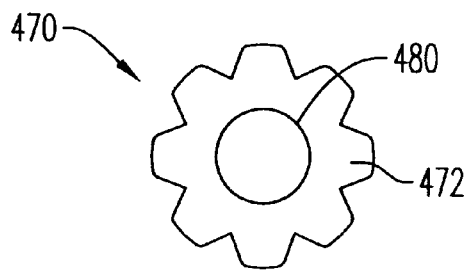
FIGS. 33 through 36 show another embodiment of the sponge of the cleaning member of the cleaning device of the invention.
Figure 33:
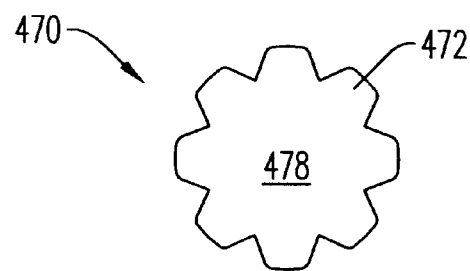
Figure 34:
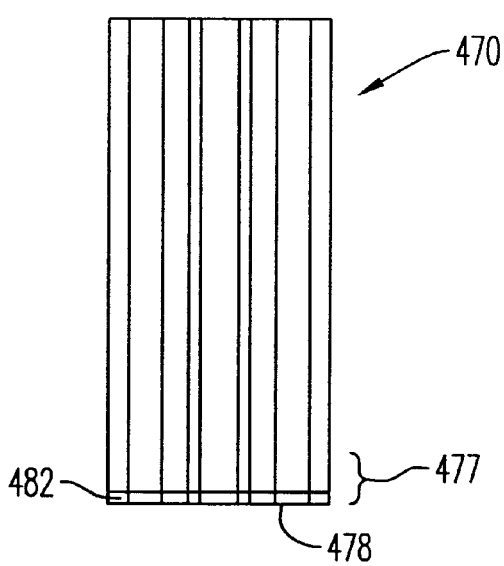
Figure 36:
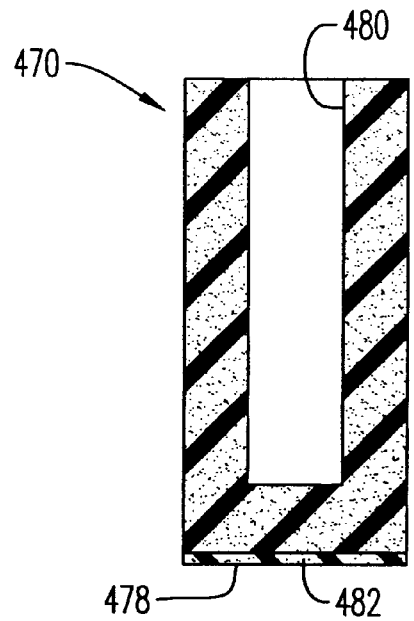
Figure 39:
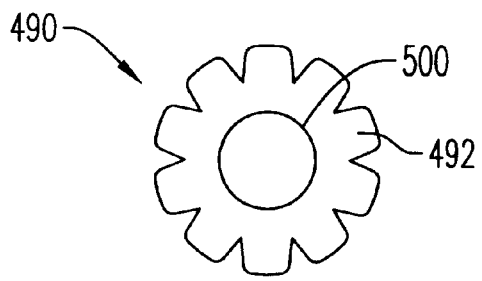
FIGS. 37 through 40 show another embodiment of the sponge of the cleaning member of the cleaning device of the invention.
Figure 37:
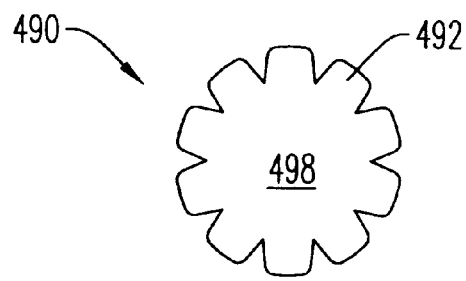
Figure 38:
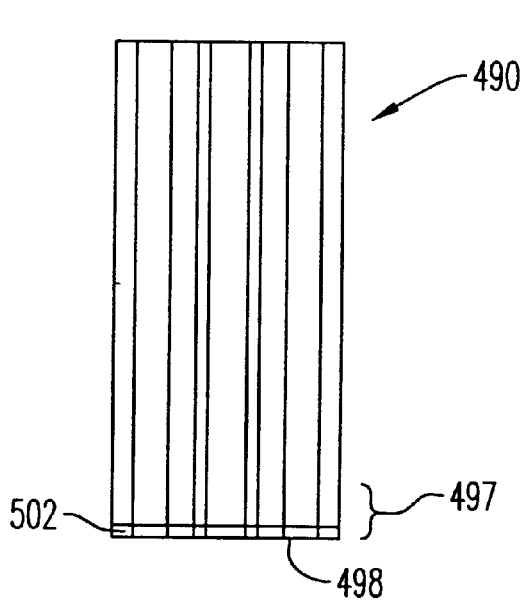
Figure 40:
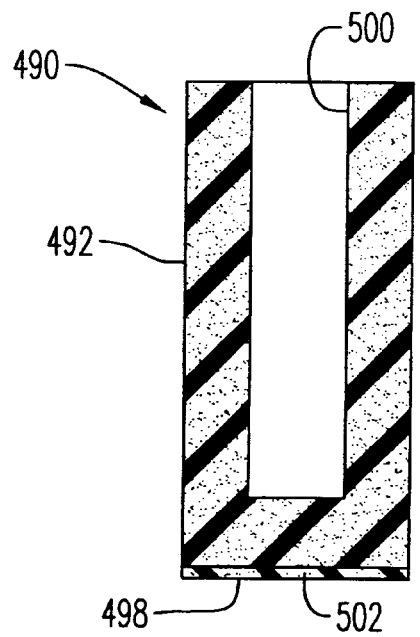

FIG. 20 show s a portion of a handle 20" having a wall whose interior surface has a radially inwardly extending annular flange 52" that extends into a channel 206'" of a nub 202'" of a nipple brush 2000, to thereby mount the nipple brush to the handle.

FIGS. 21 through 24 show the most preferred nub, generally referred to as 2002, for a nipple brush for mounting it to a handle of a cleaning device of the invention. More particularly, these Figures show that nub 2002 is comprised of a base 2004 and annular channels 2006, 2006' between and formed by distally facing surfaces 2008, 2008', neck 2010 and proximally facing surface 2113 of ring R and 2113' of head 2112. Nub 2002 has a bore 2014 for securing a stem to the nub. The outer surface of the lower portion of base 2004 has a square configuration for seating in a box seat like that referred to as 56 of handle 20 shown in FIGS. 2 and 6 through 8.

In the cleaning device of the invention, the nipple brush can be secured, preferably permanently, to the handle of the device in any suitable manner, by any suitable structure. The nub of the brush can be secured by gluing or by structure that provides a physical interference or friction hold of the brush within the handle. For example, tongue and groove, male-female and various pinning systems, e.g., by riveting through a portion of the nub or stem of the brush into a portion of the handle or vice versa, can be employed. Also, the stem of the brush can be adapted to provide securement to the handle. For example, the stem can be threaded or molded to a panel or member that is molded or held in or secured to the handle, or it can be bent orthogonally into for example an L- or other shape to interfere with a wall in the handle. Further, the proximal end of the stem can be joined to an expanding device that, when pushed through a hole in a wall of the handle, prevents the stem from being withdrawn from the hole.

FIGS. 25 through 28 show the preferred sponge configuration for mounting on the core of the cleaning device of the invention. More particularly, FIGS. 25 and 25A show a bottom end view of a sponge 430 having eight points, or petals 432 each having a flat radially outer end wall 434, obtuse angled flutes generally referred to as 436, a marginal end portion, e.g., 437, and a distal or forward end 438 (FIGS. 26 and 28). Sponge 430 has an axial dead end bore 440 and a distal end surface and/or end portion of the sponge that is treated, e.g., dipped in, spayed or coated and preferably impregnated, as at 442, with a liquid or other material, for example, a latex or other suitable filled or unfilled material, that, e.g., when dry or cured, stiffens the treated portion of the sponge and/or provides it with improved scrubbing, scouring and cleaning capability as compared to the rest of the softer main body portion of the sponge. When the bottom surface of the sponge or a portion of its marginal end portion is so treated, the liquid passes through the openings or pores of the sponge. This physically holds the material to the sponge. This holding is in addition to any chemical bonding or reaction of the liquid that occurs between the molecules of the liquid and/or fillers and the sponge material at the distal end or in the marginal end portion of the sponge. Preferably, openings or pores of the treated portion of the sponge remain open so that water or cleaning liquid can pass therethrough.

FIGS. 29 through 32 show another embodiment of a sponge, here generally referred to as 450, that can be mounted on the core of the cleaning device of the invention. Sponge 450 has five points or petals 452, a marginal end portion 457, a distal end 458, a bore 460 and a distal end surface and/or end portion 462 that is treated as sponge 430 is treated in FIGS. 25 through 38.

FIGS. 33 through 36 show another embodiment of a sponge, here referred to as 470, that can be mounted on the core of the cleaning device of the invention. Sponge 470 has eight points or petals 472, a marginal end portion 477, a distal end 478, a bore 480 and a distal end surface and/or end portion 482 that is treated as sponge 430 is treated.

FIGS. 37 through 40 show another embodiment of a sponge, here referred to as 490, that can be mounted on the core of the cleaning device of the invention. Sponge 490 has eight points or petals 492, a marginal end portion 497, a distal end 498, a bore 500 and a distal end surface and/or end portion 502 that is treated as sponge 430 is treated.

Core 100 and handle 20 can be made of any suitable structural material. Preferably, the material is a moldable material. Suitable materials include, but are not limited to, polyolefins, e.g. ethylene and propylene polymers and copolymers. The preferred material is ABS, an acrylonitrile-butadiene-styrene terpolymer. A less preferred material is a propylene polymer, e.g. polypropylene.

The handle attaching mechanism of the invention is not to be considered limited to the structure specifically disclosed herein. The extension of the core need only have one or more protuberance(s) or protruding member(s) that extend outwardly beyond the main or outer surface of the extension and that seat in and preferably engage one or more, preferably a plurality, e.g., at least one pair of opposed reliefs 25 that extend radially outwardly into inside surface 41 of wall 40, 40' of handle 20. Reliefs 25 can be selected from the group consisting of grooves, apertures, e.g. cutouts 24 and/or slots 26, and combinations of grooves and apertures, in a wall or other portion of the handle, such that axial and rotational movement of the core relative to the handle is prevented during the cleaning uses intended. Thus, the core extension need only have one protuberance that accomplishes that result. For example, the protuberance can be the configuration of an X or + shape that fits into and preferably engages a like-shaped slot in a portion of the handle. The protuberance(s) can be provided on the handle and the relief(s), e.g. aperture(s) can be provided in the core extension.

The cleaning device of the invention is advantageous for several reasons. It provides two cleaning elements on one handle, a large cleaning element that is exposed for more general use and a smaller one for more limited use that is stored and protected until used. Storing the smaller cleaning element, for example, the nipple brush, in the channel of the core of the invention helps to keep the nipple brush clean and readily available for when it is needed. The core with the larger cleaning element thereon is easily removed from the handle to expose the smaller cleaning element, and it is easily re-attached to the handle. The cleaning device permits a user to replace the larger removable cleaning element when it is worn or soiled, or to select and employ a different cleaning element to suit the application, different for example , as to material, size, diameter, length, configuration (e.g., more or less or differently shaped petals and/or flutes) or cleaning capabilities. For example, a user may utilize a long relatively narrow sponge for cleaning baby bottles, a shorter larger diameter one for cleaning spill-proof cups, or an axially rounded or tapered one for special applications. The smaller cleaning element preferably is permanently attached to the handle by any suitable means, that prevents axial, angular or rotational movement of the brush relative to the handle during cleaning uses, but not when removal of the cleaning member from the handle is desired. In the preferred embodiment shown, the nipple brush and handle are also designed and attached in a manner that preferably hermetically seals the handle at the site of attachment to preclude moisture from entering the handle. The nub of the nipple brush preferably is made of a relatively stiff material, for example, polypropylene.

Having thus described the cleaning device and handle of the present invention with particular reference to preferred embodiments thereof, it will be apparent that various changes and modifications may be made therein without departing from the spirit and scope of the invention as defined in the appended claims.

What is claimed is:

1. A cleaning device comprising:
    a handle having a proximal end and a distal end, said distal end having a wall, said wall having a recess extending axially into said distal end;

a cleaning member;

a nipple cleaning element for cleaning the interior of a nipple of the type used in connection with a baby bottle, said nipple cleaning element including:

a proximal end a and a distal end;

means for securing said nipple cleaning element to said distal end of said handle such that said proximal end of said nipple cleaning element is located in said recess of said handle and said distal end of said nipple cleaning element protrudes beyond said distal end of said handle; and a brush portion adapted to be housed in said cleaning member, said cleaning member being removably attached to said handle.

2. The cleaning device of claim 1, wherein said wall of said distal end of said handle has an inside surface and has at least one pair of opposed reliefs that extend radially outwardly into said inside surface of said wall.

3. The cleaning device of claim 2, wherein said reliefs are selected from the group consisting of grooves, apertures, and a combination of said grooves and said apertures.

4. The cleaning device of claim 1, wherein said wall of said distal end of said handle has a pair of opposed apertures extending in an axial direction through said wall.

5. A cleaning device comprising:

a handle having a proximal end and a distal end, said distal end having a wall, said wall having a recess extending axially into said distal end;

a nipple cleaning element for cleaning the interior of a nipple of the type used in connection with a baby bottle, said nipple cleaning element including:

a proximal end and a distal end; and means for securing said nipple cleaning element to said distal end of said handle such that said proximal end of said nipple cleaning element is located in said recess of said handle and said distal end of said nipple cleaning element protrudes beyond said distal end of said handle;

wherein said wall of said distal end of said handle has a pair of opposed cutouts, each cutout having an open entrance end at said distal end of said handle and extending from said entrance end in a proximal direction axially along said distal end portion of said wall.

6. A cleaning device comprising:

a handle having a proximal end and a distal end, said distal end having a wall, said wall having a recess extending axially into said distal end;

a nipple cleaning element for cleaning the interior of a nipple of the type used in connection with a baby bottle, said nipple cleaning element including:

a proximal end and a distal end; and means for securing said nipple cleaning element to said distal end of said handle such that said proximal end of said nipple cleaning element is located in said recess of said handle and said distal end of said nipple cleaning element protrudes beyond said distal end of said handle;

wherein said wall of said distal end of said handle has an inside surface having at least one pair of opposed reliefs that extend radially outwardly into said inside surface of said wall, and a pair of opposed cutouts, each cutout having an open entrance end at said distal end of said handle and extending from said entrance end in a proximal direction axially along a portion of said wall, and said pair of opposed cutouts and said pair of opposed reliefs are axially aligned with each other and axially spaced from each other along said wall of said handle.

7. A cleaning member for use with the handle of a cleaning device, comprising:

a cleaning element having an elongated axial dead end bore, and an elongated core, said core being comprised of an elongated main body having a first end, said main body being disposed in said core and being secured to said cleaning element, an extension that extends from and beyond said main body in an axial direction opposite to said first end, said extension having an open end, and an elongated channel that extends from said open end axially into the interior of said extension, said extension including a plurality of opposed axially elongated tabs, each of said plurality of tabs having an outer surface and a free end, each of said opposed tabs having a normal position and being movable from said normal position inward toward said channel and being biased to return to its said normal position, each of said opposed tabs including at least one protuberance that extends outwardly beyond said outer surface of said tab.

8. The core of claim 7, wherein said at least one protuberance extends in a transaxial direction on said tab.

9. The core of claim 8, wherein said at least one transaxial protuberance comprises a ridge.

10. The core of claim 7, wherein said at least one protuberance extends in an axial direction on said tab.

11. The core of claim 10, wherein said at least one axial protuberance comprises a pad.

12. The core of claim 7, wherein said main body of said core has an outer surface, and said outer surface of said main body has a plurality of ribs that are axially spaced from one another and that extend outward from said outer surface to engage said bore of said cleaning element and assist in securing it to said main body of said core.

13. The core of claim 7, wherein said main body of said core has a wall and said wall has a hole in it that communicates with said channel to permit drainage of liquid from said channel of said core.

14. A cleaning device comprising:

a handle, said handle having a proximal grasping end, a distal end, a distal end portion, and a wall, said wall having an interior surface that defines a recess that extends from said distal end axially into said distal end portion of said handle, said interior surface of said wall having a plurality of reliefs therein, and a cleaning member, said cleaning member being comprised of a core that is removably attached to said handle, and an elongated first cleaning element that is secured to said core, said core having a main body and an extension that extends from said main body and is disposed in said recess of said handle, said extension having a plurality of axially extending radially outwardly biased tabs, each of said plurality of tabs having an outer surface and at least one protuberance that extends radially outwardly from said outer surface and fits in and frictionally engages a said relief in said interior surface of said wall of said handle, to removably attach said cleaning member to said handle, said plurality of tabs being movable inwardly against said bias to disengage said protuberances from said reliefs and permit removal of said cleaning element from said handle.

15. The cleaning device of claim 14, wherein said first cleaning element of said cleaning member is a cylindrical sponge that is suitable for cleaning the interior of a container for feeding liquid to a baby.

16. The cleaning device of claim 14, wherein said handle includes an elongated second cleaning element having a distal end and a proximal end, said proximal end of said second cleaning element being secured to said handle within said recess such that said distal end of said cleaning element protrudes from said distal end of said handle, and wherein said extension of said core has a proximal end remote from said main body, and an elongated channel that extends from said proximal end axially into the interior of said extension, said distal end of said second cleaning element of said handle being housed in said channel of said core when said cleaning member is attached to said handle.

17. The cleaning device of claim 14, wherein said second cleaning element of said handle is a brush that is suitable for cleaning the interior of a nipple for feeding a baby.

18. The cleaning device of claim 14, wherein said plurality of reliefs in said interior surface of said wall of said handle include a pair of opposed slots through said wall of said handle.

19. The cleaning device of claim 18, wherein said distal end of said wall of said handle has a pair of opposed cutouts, each cutout being defined by an edge and having an open entrance end at said distal end of said handle and extending from said entrance end in a proximal direction along a portion of said wall, and said pair of opposed slots and said pair of opposed cutouts being axially aligned with each other and axially spaced from each other along said wall of said handle.

20. The cleaning device of claim 19, wherein each of said plurality of opposed tabs has a proximal free end, a distal end that is joined to said main body of said core, at least one said protuberance in the form of a transaxial ridge located adjacent said free end of said opposed tab, and at least one protuberance in the form of an axial pad located adjacent said distal end of said tab, said ridge and said pad on a said tab being axially aligned, and said ridge having a transaxial length and said open entrance end of said cutout having a transaxial length, the transaxial lengths of said ridges of said tabs being shorter than those of said open entrance ends of said cutouts, said ridges being chamfered to facilitate their movement axially into said open entrance ends of said cutouts, such that when said opposed tabs of said extension of said core are axially aligned with said open entrance ends of said cutouts of said handle and said core and said handle are moved axially toward one another, said ridges enter said cutouts and said edges of said cutouts engage and depress said ridges and said tabs inward toward said channel such that said ridges to enter said recess and slidingly engage said interior surface of said wall of said handle until said ridges move outwardly into and seat in said slots and said pads of said tabs enter axially into and seat in said cutouts of said handle, to removably attach said core of said cleaning element to said handle.

21. The cleaning device of claim 20, wherein said cutouts of said handle and said pads of said opposed tabs are conically shaped when seen in plan view.

22. The cleaning device of claim 21, wherein said ridges have end surfaces and portions that adjoin said end surfaces and said leading edges, said end surfaces and said adjoining portions are chamfered, and said conically shaped pads and cutouts and said chamfered adjoining portions of said ridges allow said core to be manually rotated relative to said handle to cause said interior surface of said wall of said handle to ride over said pads and said ridges and to depress said opposed tabs toward said channel and allow removal of said core from said handle without need of direct manual depression of said pads of said opposed tabs.

23. The cleaning device of claim 20, wherein said ridges have end surfaces and portions that adjoin said end surfaces and said leading edges, and said end surfaces and said adjoining portions are chamfered.

24. The cleaning device of claim 18, wherein said pair of opposed slots extend in a transaxial direction through said wall of said handle.

25. The cleaning device of claim 14, wherein said distal end of said wall of said handle has a pair of opposed cutouts, each cutout having an open entrance end at said distal end of said handle and extending from said entrance end in a proximal direction axially along a portion of said wall.

26. The cleaning device of claim 25, wherein each said cutout is conically shaped when seen in plan view.

27. The cleaning device of claim 14, wherein said at least one protuberance of each of said opposed tabs extends in a transaxial direction relative to its said tab.

28. The cleaning device of claim 27, wherein said at least one protuberance comprises a ridge.

29. The cleaning device of claim 28, wherein said ridge is rectangular when seen in plan view.

30. The cleaning device of claim 29, wherein said at least one protuberance comprises a pad.

31. The cleaning device of claim 30, wherein said pad is conically shaped when seen in plan view.

32. The cleaning device of claim 14, wherein said at least one protuberance of each of said opposed tabs extends in an axial direction on said tab.

33. The cleaning device of claim 14, wherein each of said opposed tabs has a distal end and a proximal end, and includes two said protuberances, one in the form of a ridge that extends in a transaxial direction adjacent said proximal end of said tab, and one in the form of a pad that extends in an axial direction adjacent said distal end of said tab.

34. The cleaning device of claim 33, wherein said at least one ridge is rectangular when seen in plan view.

35. A cleaning device comprising:
   a handle having a proximal end and a distal end, said distal having a recess extending axially into said distal end;
   a cleaning element located in said recess, said cleaning element being adapted to be connected to said distal end of said handle;
   a cleaning member, said cleaning member being removably attached to said handle;
   wherein said cleaning element is housed in said cleaning member when said cleaning member is attached to said handle.

* * * * *